(12) United States Patent
Karr (10) Patent No.: US 6,378,372 B1
(45) Date of Patent: Apr. 30, 2002

(54) ACOUSTIC RESONANCE ANALYSIS OF GAS MIXTURES

(76) Inventor: Lawrence J. Karr, 445 - 15th St., Santa Monica, CA (US) 90402

( * ) Notice: Subject to any disclaimer, the term of this patent is extended or adjusted under 35 U.S.C. 154(b) by 0 days.

(21) Appl. No.: 09/859,119

(22) Filed: May 15, 2001

Related U.S. Application Data (60) Provisional application No. 60/204,757, filed on May 17, 2000.

(51) Int. Cl.[7] ............................................. G01N 29/02
(52) U.S. Cl. ...................... 73/579; 73/24.01; 73/24.02; 73/597; 73/602
(58) Field of Search ........................ 73/579, 597, 598, 73/600, 602, 24.01, 24.02

(56) References Cited

U.S. PATENT DOCUMENTS

| | | | |
|---|---|---|---|
| 3,805,590 A | | 4/1974 | Ringwell et al. |
| 3,874,221 A | * | 4/1975 | Lockie ............................ 73/30 |
| 5,060,506 A | | 10/1991 | Douglas ..................... 73/24.01 |
| 5,060,507 A | * | 10/1991 | Urmson et al. ............. 73/24.01 |
| 5,285,675 A | * | 2/1994 | Colgate et al. .............. 73/23.2 |
| 5,351,522 A | | 10/1994 | Lura .......................... 73/24.01 |
| 5,392,635 A | * | 2/1995 | Cadet et al. ................ 73/24.01 |
| 5,473,934 A | * | 12/1995 | Cobb .......................... 73/61.49 |
| 5,501,098 A | * | 3/1996 | Cadet et al. ................ 73/24.01 |
| 5,625,140 A | | 4/1997 | Cadet et al. ................ 73/24.01 |
| 5,627,323 A | * | 5/1997 | Stern ....................... 73/861.28 |
| 5,768,937 A | * | 6/1998 | Wajid et al. ................ 73/24.06 |
| 6,192,739 B1 | * | 2/2001 | Logue et al. ............... 73/24.01 |

* cited by examiner

Primary Examiner—Hezron Williams
Assistant Examiner—Jacques Saint-Surin
(74) Attorney, Agent, or Firm—Thomas I. Rozsa; Tony D. Chen (57) ABSTRACT

An acoustic device for continuously or intermittently determining the composition of gas mixtures. The acoustic device has an acoustic resonator with input and output transducers arranged to minimize the effect of external conditions. The device normally operates as a feedback oscillator with the oscillation frequency determined by the gas-filled resonator's natural frequency, providing a speed of sound measurement. The device is configured as two open ended parallel side by side adjacent one half wavelength tubes, each with sending and receiving transducers inserted through a tube wall at the midpoint of that tube. This forms a symmetric quarter wave resonator from each tube. The two sending transducers are operated out of phase, as are the two receiving transducers. The causes cancellation of external sounds, and of their influence on measurements. A small pressure relieved cap is preferably placed over the external surface of each transducer. This farther reduces radiated sound and makes the effective resonator length essentially independent of the gas mixture's acoustic impedance, allowing operation over a wide pressure range. A simple electronic circuit provides appropriate differential gain, amplitude control, and phase shift, achieving steady oscillation. Determination of gas mixtures is by computation from frequency and temperature measurements, with real gas corrections as necessary.

34 Claims, 5 Drawing Sheets

ACOUSTIC RESONANCE ANALYSIS OF GAS MIXTURES

This Patent Application claims the priority of prior U.S. Provisional Patent Application Serial Number 60/204,757, Filed on May 17, 2000.

BACKGROUND OF THE INVENTION

1. Field of the Invention

The present invention relates generally to the field of acoustic gas monitoring and more specifically to monitoring, at various pressures, of gas mixtures used for diving, medical purposes, or in related industries.

2. Description of the Prior Art

In many applications it is necessary to determine the composition of gas mixtures used for breathing or for anesthesia purposes, for example. Conventional techniques typically employ wet chemistry, mass spectrometry, infrared techniques, galvanic fuel cells, or even paramagnetism.

In many situations, such as with breathing mixtures, one is concerned only with two component gases. When this is the case, one doesn't need a measurement system specific to a particular gas, since the gases are specified, and it is only the fraction that needs determination. In other cases, it is possible to treat as binary gases, mixtures which aren't binary. This occurs when some of constituent gases are present in fixed rations. An example of this would be a mixture of dry air plus pure oxygen. The composition of dry air is known, so the addition of pure oxygen allows the resulting mixture to be analyzed by binary gas technique.

A very important area of gas monitoring is in general for breathing gases. In medical applications, oxygen is frequently added to air. Sophisticated SCUBA diving is now done with NITROX, which is oxygen enriched air. The existing inexpensive oxygen monitors in use are typically electrochemical devices, either fuel cells or polarigraphic half cells. Those devices have a limited life time and require frequent recalibration. More importantly, such prior art devices have severe temperature dependence, and can only be approximately compensated for temperature. In diving or other hyperbaric applications, the fuel cells are commonly used. These devices have semi-permeable membranes, which frequently malfunction under pressure, and result in false indications. Further, the membranes, if they become wet, will now sense the dissolved oxygen level in the surface liquid rather than in the gas mixture. For these reasons, it is common practice to use triple redundant fuel cells in rebreathers for divers.

Acoustical methods have been employed for at least a century for gas analysis. An early application of acoustic technique to gas analysis was the detector used in mines at the beginning of the $20^{th}$ century. This device was an automatically actuated double whistle, one unit filled with pure air, the other with the air from the mine. The velocity of sound in a gas is function of temperature and gas composition. Since the whistles were of identical construction and at equal temperature, any difference in pitch of the two whistles was due to potentially dangerous contamination of the mine air supply. Very small differences in frequency could be perceived as a "beat note". Thus the extent of explosive and/or toxic fumes could be estimated.

Most existing acoustic methods of gas analysis have used either time-of-flight method (see, e.g., U.S. Pat. Nos. 5,060,506, 5,351,522, and 5,625,140) or phase shift method (see e.g., U.S. Pat. No. 3,805,590). In fact, the time-of-flight patents are quite concerned with minimizing sound reflections and standing waves. The time-of-flight methods are inherently pulsed, since a time interval must have a beginning and an end. U.S. Pat. No. 3,805,590 is concerned with a binary mixture of helium and oxygen where the speed of sound varies greatly as a function of concentration, allowing very approximate measurement techniques to provide adequate performance. The pulsed time-of-flight methods may require multiple calibration points to compensate for the variation in the response of the transducers.

These existing devices are also sensitive to the ambient pressure, as the acoustic impedance of the gas changes linearly with density. Pulse devices also suffer from an inherently low signal to noise ratio, as the acoustic energy in a short pulse is small. This low signal-to-noise ratio may cause measurement errors. Further, the resonant piezoelectric transducers in many of these devices are themselves not temperature stable, and may even suffer drift over a time period, requiring-re-calibration.

It is therefore desirable to introduce and develop a new method for analyzing gas mixtures.

SUMMARY OF THE INVENTION

The present invention is a unique and novel method for analyzing gas mixtures.

Described generally, the present invention is an apparatus for gas mixture analysis. The analyzing apparatus includes a symmetric acoustic resonating device for generating quarter-wave mode acoustic resonance in its hollow chamber which is filled with a gas mixture.

The symmetric acoustic resonating device includes a pair of parallel elongated tubes each having a hollow chamber with two opposite open ends. The symmetric acoustic resonating device also includes a pair of receiving transducers each mounted at an aperture located at the middle of a respective one of the two elongated tubes, such that the pair of receiving transducers are adjacent to each other, and a pair of transmitting transducers each mounted at an aperture also located at the middle of a respective one of the two elongated tubes, such that the pair of transmitting transducers are opposite to each other. The symmetric acoustic resonating device further includes an electronic circuitry connected between the pair of receiving transducers and the pair of transmitting transducers for producing a desired acoustic resonance in the hollow chambers of the elongated tubes for determining the composition of gas mixtures contained in the hollow chambers.

The analyzing apparatus also includes a temperature sensor for measuring the temperature of said gas mixture. The analyzing apparatus further includes a counter-timer for measuring the frequency of said acoustic resonance. The temperature and frequency measurements are used for analyzing the composition of the gas mixture.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
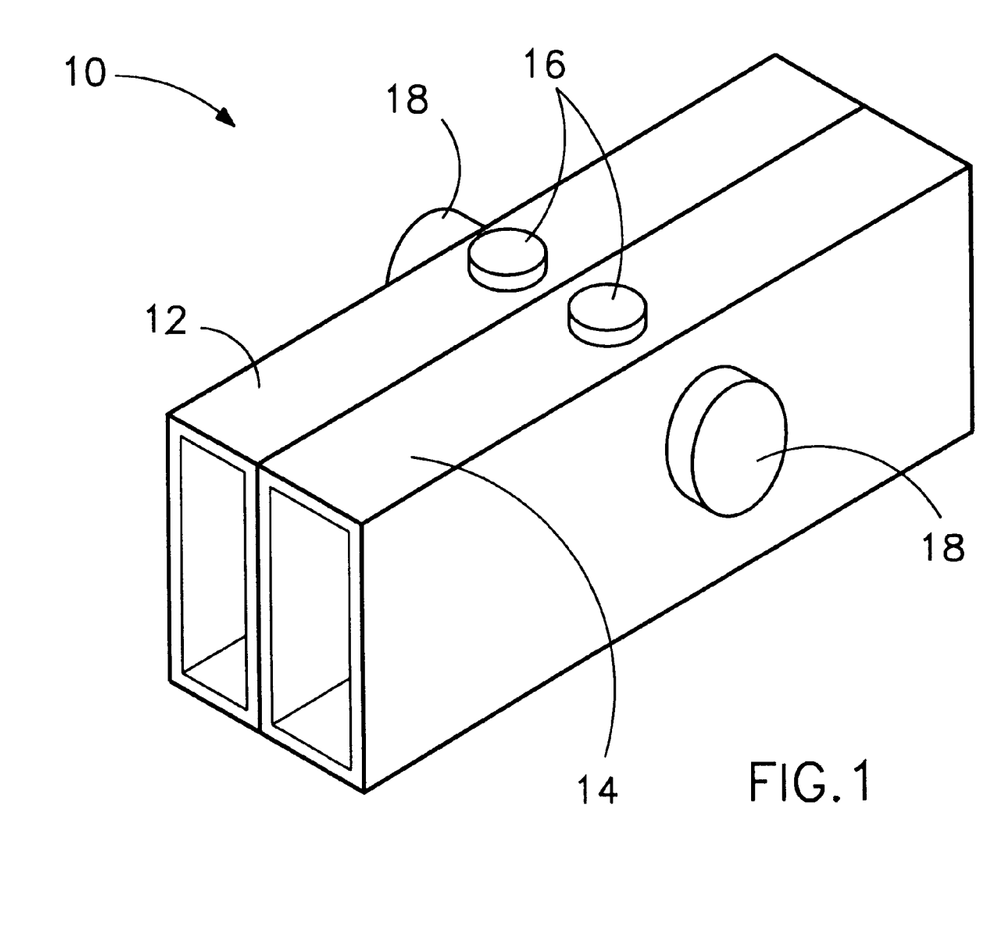
FIG. 1 is a perspective view of a present invention acoustic resonance device.

The present invention is directed to an acoustic gas composition analysis system which includes a resonance device 10. The resonance device 10 includes a pair of symmetric quarter wave resonators 12 and 14 which are used as the frequency determining elements in an oscillator, whose nominal frequency is the velocity of sound divided by four times the effective resonator length. Each of the resonators 12 or 14 consists of tubes open at both ends, and with receiving acoustic transducers 16 and transmitting acoustic transducers 18 mounted midway between the open ends. The two tubes 12 and 14 are driven in phase opposition, and the receiving transducer signals are electrically subtracted, producing a difference signal.

The transducers 16 and 18 are mounted through holes in the tubes, which are rectangular in cross section, with wide and narrow sides. The receiving transducers 16 and transmitting transducers 18 are generally operated in a non-resonant mode.

Typically the receiving transducer 16 would be an omnidirectional electret condenser microphone mounted through the narrow tube wall. Typically the transmitting transducer 18 would be a miniature dynamic loudspeaker mounted through an adjacent wide wall of the same tube, so that both transducers are placed at the exact centers of the open tubes.

To achieve maximum external sound cancellation, the rectangular tubes are arranged so that the wide tube sides are adjacent, bringing the centers of the tube ends as close together as practicable. In this configuration, the loudspeakers are placed on the opposite wide sides, and the microphones are placed on adjoining short sides of the two tubes. This type of resonant system with dynamic loudspeakers and omnidirectional electret condenser microphones normally exhibits a phase shift at resonance of 90 degrees between the electrical signal to a speaker and the electrical output of the corresponding microphone. A corresponding 90 degree shift must be introduced into the electronics to achieve oscillation at the center frequency.

Figure 2:
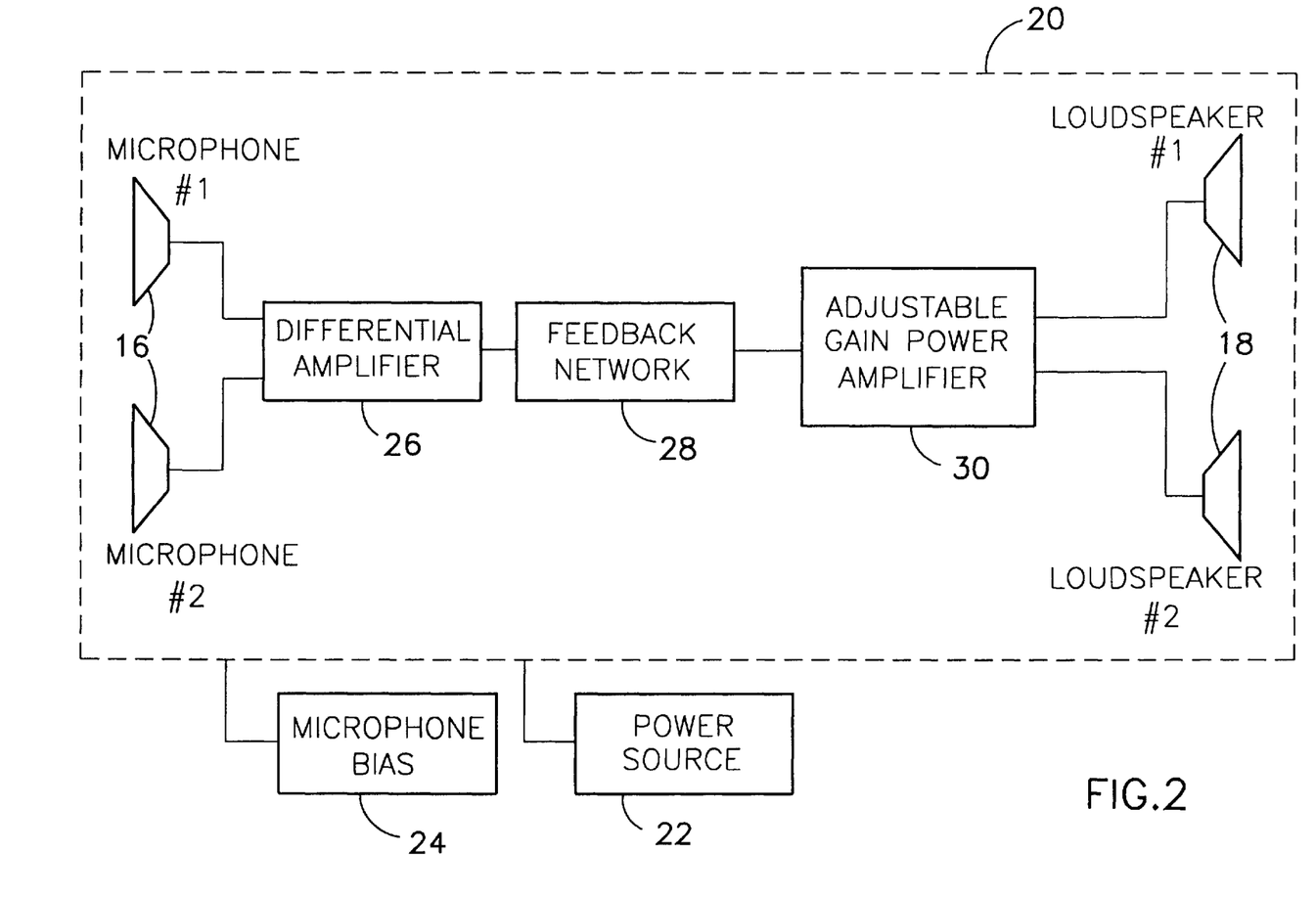
FIG. 2 is a schematic block diagram of the present invention acoustic resonance device.

Referring to FIG. 2, there is shown a block diagram of an exemplary electronic circuitry of the resonance device 10.

The electronic circuitry of the resonance device 10 includes a main circuit 20 powered by a power source component 22 and biased by a microphone bias component 24. The main circuit 20 further includes the two microphones 16, a differential amplifier component 26, a modified feedback integrator network component 28, an adjustable gain power amplifier component 30, and two loudspeakers 18.

Referring to FIGS. 2, 3, 4(a), 4(b) and 4(c), there is shown a preferred embodiment of the exemplary electronic circuitry of the resonance device 10.

Figure 4A:
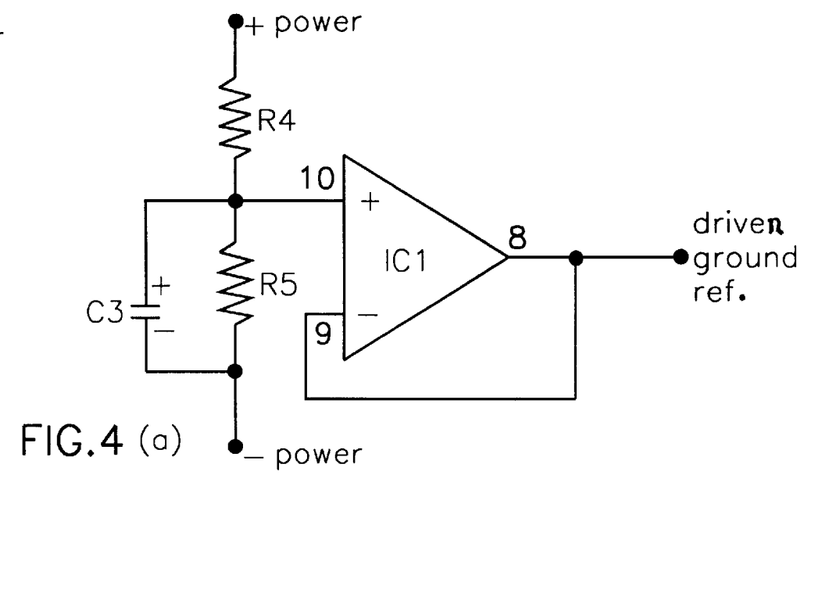
FIG. 4(a) is an exemplary circuitry diagram of a power source component of the present invention acoustic resonance device.
Figure 4B:
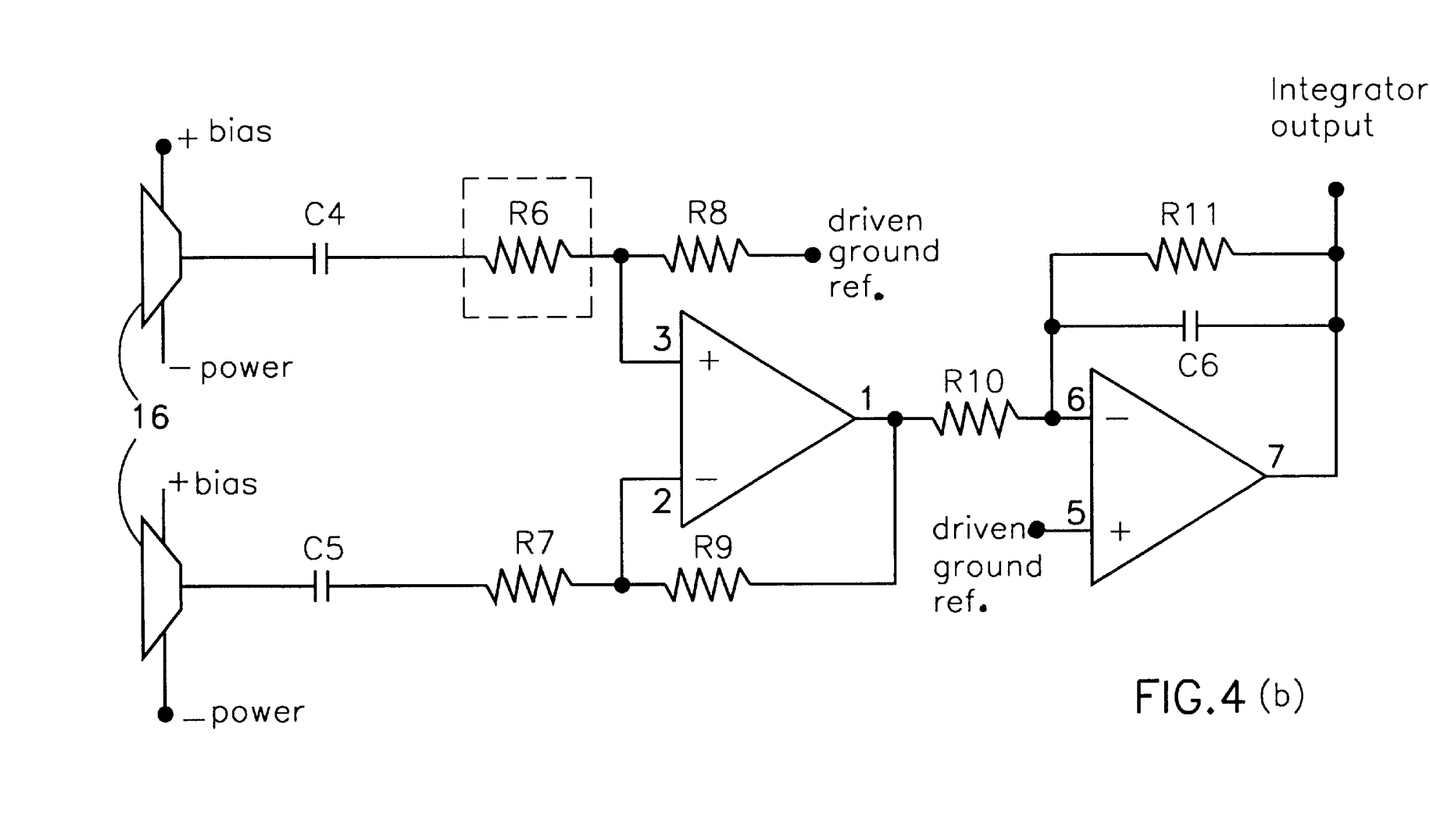
FIG. 4(b) is an exemplary circuitry diagram of a differential amplifier component and a modified feedback integrator network component of the present invention acoustic resonance device.

In this embodiment, the microphone output signals are electronically subtracted with the differential amplifier circuit 26. The differential amplifier circuit 26 operates as a trimming means to exactly balance the microphone sensitivities to achieve optimum rejection of external sounds. The output of the differential amplifier 26 is in a preferred embodiment applied to the input resistor of a modified feedback integrator 28. The modified feedback integrator 28 has a high resistance resistor shunting its integrating feedback capacitor, which limits the DC gain to minus the ratio of the shunt resistor to the input resistor. The integrator 28 provides a nominal 90 degree phase shift, and also a 6 decibel per octave frequency roll-off.

Figure 4C:
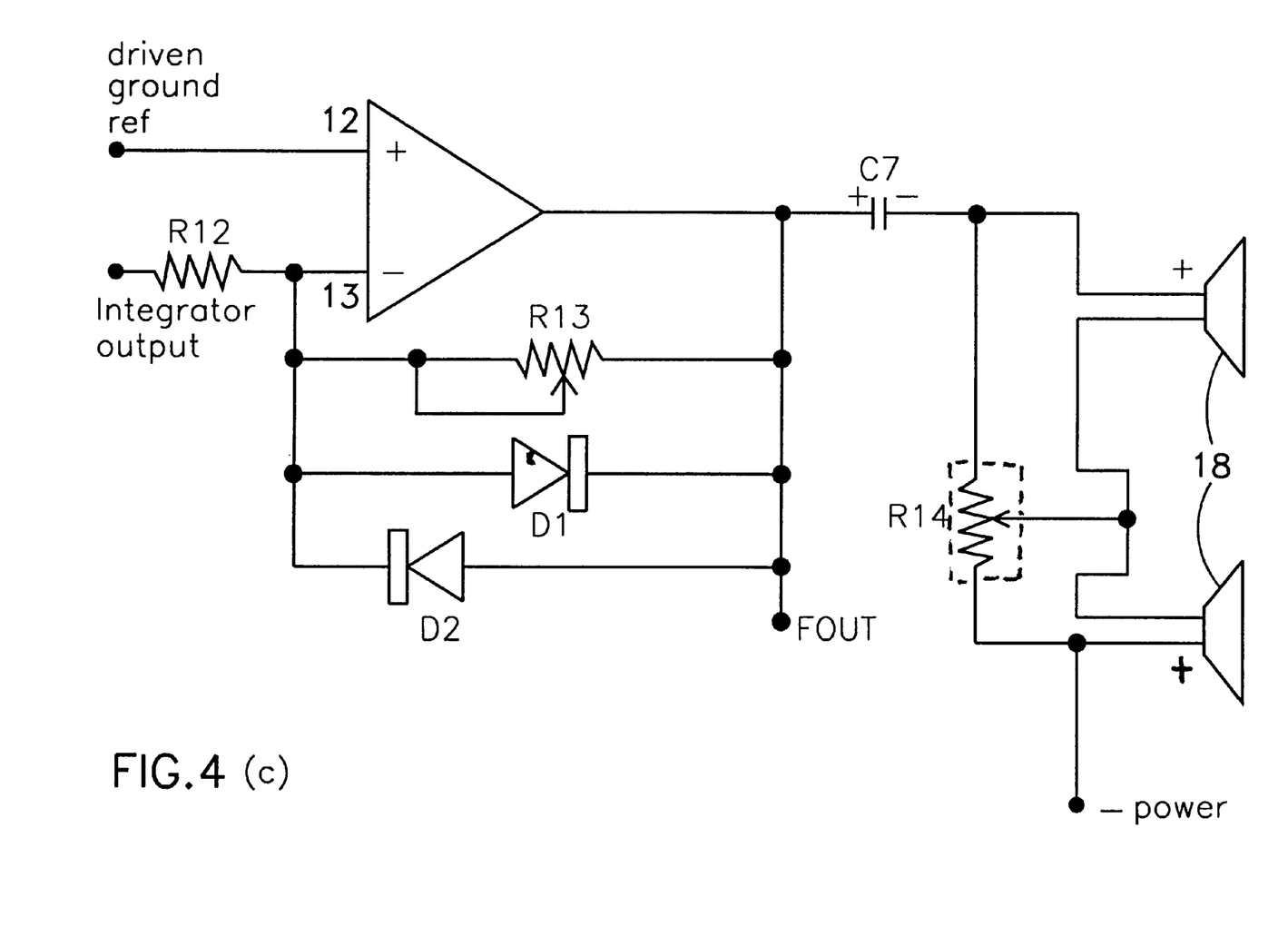
FIG. 4(c) is an exemplary circuitry diagram of an adjustable gain power amplifier component of the present invention acoustic resonance device.

The output of the modified integration, in the preferred embodiment, is connected to the input of the soft clipping adjustable gain power amplifier 30 which differentially drives the two loudspeakers 18. This is easily done by connecting the two loudspeakers 18 either in series or parallel so that they are driven in phase opposition to each other. This loudspeaker drive arrangement may have provision for adjusting the relative signal levels to the loudspeakers 18 so that they produce equal and opposite phase outputs, reducing the sound radiation from the apparatus.

With this configuration, and with the transducers 16 and 18 connected in the proper phase, an oscillation in the quarter wave mode is produced. The higher frequency modes (¾, 5/4, 7/4 wave, etc.) are suppressed because of the 1/f amplitude characteristic of the modified feedback integrator 28. Thus, an essentially sinusoidal integrator output is produced. The provision of an anti-parallel pair of diodes shunting the power amplifier feedback resistor causes this oscillation to be of essentially constant amplitude, and makes the sound power independent of the voltage of the power supply circuitries 22 and 24.

Figure 3:
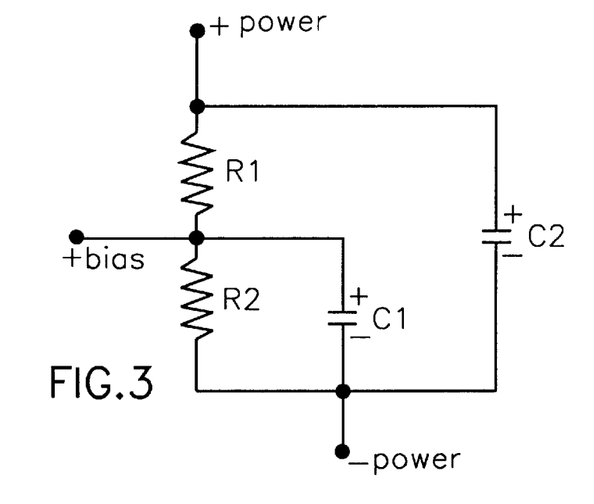
FIG. 3 is an exemplary circuitry diagram of a bias component of the present invention acoustic resonance device.

The following values are provided by way of example only:

In the microphone bias component 22, resistor R1 is 5.6 kΩ, resistor R2 is 1 kΩ, capacitor C1 is 10μF, and capacitor C2 is 10μF.

In the power source component 24, resistor R4 is 20 kΩ, and resistor R5 is 20 kΩ.

In the differential amplifier component 26 and feedback integrator component 28, resistor R6 is 200 kΩ, resistor R7 is 200 kΩ, resistor R8 is 200 kΩ, resistor R9 is 200 kΩ, resistor R10 is 30 kΩ, resistor R11 is 1 MΩ, capacitor C4 is 0.022 μF, capacitor C5 is 0.022μF, and capacitor C6 is 1,000 pF.

In the adjustable gain power amplifier component 30, resistor R12 is 20 kΩ, resistor R13 is 100 kΩ, and capacitor C7 is 22 μF.

The operational amplifier used in the circuitry 20 is a LMC6484 chip, and diodes D1 and D2 are 1N4148 diodes.

It is noted that the power source may utilize a single 9 volt alkaline battery, which may be a type MN1604 battery.

It is also noted that resistor R6 is used for optional microphone gain balance trim value to null external sounds at pin 1 of the LMC6484 chip.

It is additionally noted that adjustable resistor R14 is used for optional loudspeaker gain balance. This may be done by install and adjust 100 Ω trim value to minimize operating sound radiation.

It is further noted that connections to the first terminals (terminals "A") of the two loudspeakers 16 may need to be exchanged, whereby correct connection will cause approximately 2 kHz oscillation.

With changes in gas density, the reflection and transmission of sound off/through the transducer diaphragms changes. In general, the extent to which sound waves are reflected from a thin diaphragm diminishes as a function of gas density, and transmission through a thin diaphragm increases as a function of gas density. This relationship can change the effective resonator geometry, resulting in substantial changes in resonant frequency as a function of gas density. This may cause an error in the analysis of a given gas mixture as it's pressure increases. To minimize this effect, omni-directional microphones with caps on the far sides of the vented diaphragms are used. The capped microphones provide a fixed geometry. Similarly, a cap with pressure venting is placed over the back side of each loudspeaker. This stabilizes the effective resonator length as a function of gas pressure.

Alternatively, a loudspeaker with a small pressure venting hole may be used with a completely closed cap. The commonly plugged vent in the speakers pole piece is preferably left open, as otherwise the air spring resulting from the tiny trapped volume becomes excessively stiff at high ambient pressures.

A temperature sensor is used to measure the gas temperature. It is convenient to use a thermistor or other electronic sensor such as a National Semiconductor LM-35 temperature sensor. This temperature sensor can be mounted to the external surface(s) of the resonator(s). With this, the gas temperature can be compensated. The frequency of oscillation varies as the square root of the absolute temperature. A microcontroller, for example an INTEL 87C196KD, fitted with an Analog/Digital (A/D) converter, in a preferred embodiment, can acquire the temperature information. The same microcontroller equipped with counters and timers, can measure the period of some number of oscillations, or can simply count the input frequency. In this way, the frequency can be precisely measured, given that the microcontroller uses a quartz crystal as it's timing source. The temperature needs to be measured with good repeatability and linearity, but not extreme absolute accuracy. The speed of sound in gas is predicted to be $$c = \text{square root of } (\gamma RT/M) \quad [1]$$

where gamma ($\gamma$) is the ratio of specific heats, which is about 1.402 for air, R is the universal gas constant, T is the temperature in degrees Kelvin, and M is the kilogram molecular weight of the gas.

For air, this gives an expected velocity of $$c = \text{square root of } ((1.402 \cdot 8.3143(J/\text{mole}^\circ K) \cdot 273^\circ K)/(0.028965(kg/\text{mole}))) \quad [2]$$

or 331.5 meters per second.

With simple algebra, it is possible to compute the velocity of sound for various gasses and mixtures. It is then possible to write an equation for the composition of a binary gas mixture as a function of the speed of sound in that mixture. The frequency of oscillation for a one quarter wave oscillator of this type is the velocity of sound divided by four times the effective resonator length. Thus, a device of this type with tubes of 7.62 cm length, would have a physical resonator length of 3.81 cm. This would give a predicted frequency in 19 degree Kelvin air of about 2,250 Hz. The effective resonator length was found in an actual case to be about 4.20 cm.

As an example, the present invention resonance device 10 may be constructed with a resonator formed of two rectangular steel tubes of internal cross section 2.36 cm by 1.08 cm. These tubes are 7.62 cm long. The two tubes, of thin wall construction, each have two holes in them, one hole, of 15.17 mm diameter at the midpoint of the tube on the centerline of the 2.36 cm face, and the other hole of 6.16 mm diameter at the tube midpoint on the centerline of the 1.08 cm face. The two tubes are soldered together, bonding the 2.36 cm width faces that are not drilled, along their length. This forms an assembly of approximately square cross section, with two adjacent rectangular openings at either end.

The dynamic drivers from a pair of Radio Shack Stereo Headphones, model 33-1133, were fitted to the 15.17 mm holes, closing those holes with their diaphragms. These drivers were modified, removing the sealant from the holes in the center magnetic pole pieces. Cylindrical caps of 5 mm depth with small vent holes were affixed to the backs of the drivers, and the lead wires brought out through these small vents. This allowed for pressure relief and gas exchange into these small volumes. GENTEX model 3307-2 electret microphone elements were fitted to the 6.16 mm holes. The transducers were affixed with super glue. The transducers are connected to the circuitry 20.

A National Semiconductor LM35 temperature sensor was used to measure resonator temperature. A data acquisition board installed in a personal computer was used to digitize the output of the temperature sensor, and to measure, by means of period averaging counters, the oscillation frequency of the resonator assembly. The output of the power amplifier stage was connected to an appropriately biased Schmitt trigger, which was connected to the counter-timer input. The counters can be connected to record the time between a programmable number of zero crossings of either of both polarities. If, for instance, the unit is programmed to record the elapsed time between the first and the one hundredth positive going zero crossing, then microsecond, then the frequency resolution is approximately 0.04 Hz for a 2 kHz center frequency. Other means may of course be used for frequency measurement. For the sample device, it was determined that a good measure of Oxygen concentration in Oxygen-Nitrogen mixtures was to say that:

$$FO_2 = 7.5472\eta - 7.337 \quad [3]$$

where $$\eta = (T/T_{ref}) \cdot (f_{ref}/f)^2 \cdot (1 - 24 \times 10^{-6} \cdot (T - T_{ref})) \quad [4]$$

In these equations, the factor of 24 parts per million is twice the coefficient of linear expansion of steel, which is the resonator tube material. In all cases here, temperature is in degrees Kelvin. The reference here was dry air at 1 atmosphere absolute pressure and 292.3 degrees Kelvin. The reference frequency ($f_{ref}$) was 2,040.35 Hz. This equation was able to predict oxygen fraction to within about 0.005 over temperatures from 278 Kelvin to 303 Kelvin and oxygen fractions from 0.209 to 1.00.

It was found that the sample sensor shows some slight pressure sensitivity, which is due to real gas effects. This sensitivity can be largely eliminated by adding terms to the gas fraction equation to compensate for variation of gamma with ambient pressure. The resulting device is able to measure oxygen fraction accurately over pressures from 1 bar to 5 bar absolute. Clearly it is possible to replace the personal computer and data acquisition board with a microcontroller to produce a compact low-cost oxygen sensor.

The present invention gas analyzing device described here required only a single point calibration at a reference temperature and gas mixture, and operates over a wide range of concentrations, temperatures and pressures. In fact, the sensor may be used with other gasses after calibration for a gas, since the calibration is largely for the temperature sensor and the exact resonator dimensions. This may allow its use as, for example, a gas mixture verification device when using gas blends for medical purposes. The device would need only an expected sound velocity for a gas at a given temperature, and could return a plausibility check.

The present invention arrangement has many advantages. Since the resonator tubes are open at both ends, gas can rapidly fill them, resulting in quick measurements. This configuration, with its closely adjacent opposite phase sources, greatly reduces radiated sound, and the influence of external objects. The acoustic receiving transducers in phase opposition greatly reduce any sensitivity to outside acoustic noise, in the manner of a noise canceling microphone. This has the further salutary effect of improving the accuracy of the resulting sensor.

Defined in detail, the present invention is an acoustic resonance device used for gas mixture analysis, comprising: (a) a pair of parallel elongated tubes each having a hollow chamber with two opposite open ends; (b) a pair of receiving transducers each mounted at an aperture located at the middle of a respective one of the two elongated tubes, such that the pair of receiving transducers are adjacent to each other; (c) a pair of transmitting transducers each mounted at an aperture also located at the middle of a respective one of the two elongated tubes, such that the pair of transmitting transducers are opposite to each other; and (d) an electronic circuitry connected between the pair of receiving transducers and the pair of transmitting transducers for producing a desired acoustic resonance in the hollow chambers of the elongated tubes for determining the composition of gas mixtures contained in the hollow chambers.

Defined alternatively, the present invention is an apparatus for gas mixture analysis, comprising: (a) a symmetric acoustic resonating device for generating quarter-wave mode acoustic resonance in its hollow chamber which is filled with a gas mixture; (b) means for measuring the temperature of the gas mixture; and (c) means for measuring the frequency of the acoustic resonance; (d) whereby the temperature and frequency measurements are used for analyzing the composition of the gas mixture.

Defined more broadly, the present invention is an apparatus for gas mixture analysis, comprising: (a) a symmetric acoustic resonating device for generating acoustic resonance in its hollow chamber which is filled with a gas mixture; and (b) means for analyzing the composition of the gas mixture based on the acoustic resonance.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. An acoustic resonance device used for gas mixture analysis, comprising:
    a. a pair of parallel elongated tubes each having a hollow chamber with two opposite open ends;
    b. a pair of receiving transducers each mounted at an aperture located at the middle of a respective one of said two elongated tubes, such that the pair of receiving transducers are adjacent to each other;
    c. a pair of transmitting transducers each mounted at an aperture also located at the middle of a respective one of said two elongated tubes, such that the pair of transmitting transducers are opposite to each other; and
    d. an electronic circuitry connected between said pair of receiving transducers and said pair of transmitting transducers for producing a desired acoustic resonance in said hollow chambers of said elongated tubes for determining the composition of gas mixtures contained in said hollow chambers.

2. The device in accordance with claim 1, wherein said elongated tubes each has a pair of oppositely disposed elongated narrow sidewalls and a pair of oppositely disposed elongated wide sidewalls forming a rectangular shaped hollow tube.

3. The device in accordance with claim 2, wherein said two rectangular shaped hollow tubes are positioned in parallel with their adjacent wide sidewalls affixed together and their spaced apart wide sidewalls exposed.

4. The device in accordance with claim 3, wherein said pair of receiving transducers are each mounted on a narrow sidewall of a respective one of said two tubes.

5. The device in accordance with claim 3, wherein said pair of transmitting transducers are each mounted on an exposed wide sidewall of a respective one of said two tubes such that said two transmitting transducer are positioned spaced apart and oppositely.

6. The device in accordance with claim 1, wherein said receiving transducers are operated in phase opposition.

7. The device in accordance with claim 1, wherein said transmitting transducers are operated in phase opposition.

8. The device in accordance with claim 1, wherein said receiving transducers are omnidirectional electret condenser microphones.

9. The device in accordance with claim 1, wherein said transmitting transducers are miniature dynamic loudspeakers.

10. The device in accordance with claim 1 produces acoustic resonance in quarter wave modes.

11. An apparatus for gas mixture analysis, comprising:
    a. a symmetric acoustic resonating device for generating quarter-wave mode acoustic resonance in its hollow chamber which is filled with a gas mixture, further comprising:
        i. a pair of parallel elongated tubes each having a hollow chamber with two opposite open ends;
        ii. a pair of receiving transducers each mounted at an aperture located at the middle of a respective one of said two elongated tubes, such that the pair of receiving transducers are adjacent to each other;

iii. a pair of transmitting transducers each mounted at an aperture also located at the middle of a respective one of said two elongated tubes, such that the pair of transmitting transducers are opposite to each other; and iv. an electronic circuitry connected between said pair of receiving transducers and said pair of transmitting transducers for producing a desired acoustic resonance in said hollow chambers of said elongated tubes for determining the composition of gas mixtures contained in said hollow chambers;

b. means for measuring the temperature of said gas mixture; and c. means for measuring the frequency of said acoustic resonance;

d. whereby said temperature and frequency measurements are used for analyzing the composition of said gas mixture.

12. The apparatus in accordance with claim 11, wherein said elongated tubes each has a pair of oppositely disposed elongated narrow sidewalls and a pair of oppositely disposed elongated wide sidewalls forming a rectangular shaped hollow tube.

13. The apparatus in accordance with claim 12, wherein said two rectangular shaped hollow tubes are positioned in parallel with their adjacent wide sidewalls are affixed together and their spaced apart wide sidewalls exposed.

14. The apparatus in accordance with claim 13, wherein said pair of receiving transducers are each mounted on a narrow sidewall of a respective one of said two tubes such that said two receiving transducer are positioned side-by-side.

15. The apparatus in accordance with claim 13, wherein said pair of transmitting transducers are each mounted on an exposed wide sidewall of a respective one of said two tubes such that said two transmitting transducer are positioned spaced apart and oppositely.

16. The apparatus in accordance with claim 11, wherein said receiving transducers are operated in phase opposition.

17. The apparatus in accordance with claim 11, wherein said transmitting transducers are operated in phase opposition.

18. The apparatus in accordance with claim 11, wherein said receiving transducers are omnidirectional electret condenser microphones.

19. The apparatus in accordance with claim 11, wherein said transmitting transducers are miniature dynamic loudspeakers.

20. The apparatus in accordance with claim 11, wherein said temperature measuring means is a temperature sensor.

21. The apparatus in accordance with claim 11, wherein said frequency measuring means is a programmable countertimer.

22. The apparatus in accordance with claim 21, wherein said receiving transducers are operated in phase opposition.

23. The apparatus in accordance with claim 21, wherein said transmitting transducers are operated in phase opposition.

24. The apparatus in accordance with claim 21, wherein said receiving transducers are omnidirectional electret condenser microphones.

25. The apparatus in accordance with claim 21, wherein said transmitting transducers are miniature dynamic loudspeakers.

26. The device in accordance with claim 21 produces acoustic resonance in quarter wave modes.

27. The apparatus in accordance with claim 21, wherein said analyzing means comprises:

a. means for measuring the temperature of said gas mixture; and b. means for measuring the frequency of said acoustic resonance;

c. whereby said temperature and frequency measurements are used for analyzing the composition of said gas mixture.

28. The apparatus in accordance with claim 27, wherein said temperature measuring means is a temperature sensor.

29. The apparatus in accordance with claim 27, wherein said frequency measuring means is a programmable countertimer.

30. An apparatus for gas mixture analysis, comprising:

a. a symmetric acoustic resonating device for generating acoustic resonance in its hollow chamber which is filled with a gas mixture, farther comprising i. a pair of parallel elongated tubes each having a hollow chamber with two opposite open ends;

ii. a pair of receiving transducers each mounted at an aperture located at the middle of a respective one of said two elongated tubes, such that the pair of receiving transducers are adjacent to each other;

iii. a pair of transmitting transducers each mounted at an aperture also located at the middle of a respective one of said two elongated tubes, such that the pair of transmitting transducers are opposite to each other; and iv. an electronic circuitry connected between said pair of receiving transducers and said pair of transmitting transducers for producing a desired acoustic resonance in said hollow chambers of said elongated tubes for determining the composition of gas mixtures contained in said hollow chambers; and b. means for analyzing the composition of said gas mixture based on said acoustic resonance.

31. The apparatus in accordance with claim 30, wherein said elongated tubes each has a pair of oppositely disposed elongated narrow sidewalls and a pair of oppositely disposed elongated wide sidewalls forming a rectangular shaped hollow tube.

32. The apparatus in accordance with claim 31, wherein said two rectangular shaped hollow tubes are positioned in parallel with their adjacent wide sidewalls are affixed together and their spaced apart wide sidewalls exposed.

33. The apparatus in accordance with claim 32, wherein said pair of receiving transducers are each mounted on a narrow sidewall of a respective one of said two tubes such that said two receiving transducer are positioned side-by-side.

34. The apparatus in accordance with claim 32, wherein said pair of transmitting transducers are each mounted on an exposed wide sidewall of a respective one of said two tubes such that said two transmitting transducer are positioned spaced apart and oppositely.

* * * * *